(12) United States Patent
Song et al.

(10) Patent No.: US 12,097,255 B2
(45) Date of Patent: Sep. 24, 2024

(54) RECOMBINANT PORCINE PARVOVIRUS ANTIGENIC PROTEIN AND USE THEREOF

(71) Applicants: REPUBLIC OF KOREA(ANIMAL AND PLANT QUARANTINE AGENCY), Gyeongsangbuk-do (KR); BIOAPPLICATIONS INC., Gyeongsangbuk-do (KR)

(72) Inventors: Jae-Young Song, Gyeonggi-do (KR); In-Ohk Ouh, Gyeongsangbuk-do (KR); Soodong Cho, Gyeonggi-do (KR); Yongjik Lee, Gyeongsangbuk-do (KR); Ju-Yeon Lee, Gyeongsangbuk-Do (KR); In-Soo Cho, Seoul (KR)

(73) Assignees: REPUBLIC OF KOREA (ANIMAL AND PLANT QUARANTINE AGENCY), Gyeongsangbuk-do (KR); BIOAPPLICATIONS INC., Gyeongsangbuk-do (KR)

( * ) Notice: Subject to any disclaimer, the term of this patent is extended or adjusted under 35 U.S.C. 154(b) by 677 days.

(21) Appl. No.: 17/298,070

(22) PCT Filed: Nov. 15, 2019

(86) PCT No.: PCT/KR2019/015705
§ 371 (c)(1),
(2) Date: May 28, 2021

(87) PCT Pub. No.: WO2020/116815
PCT Pub. Date: Jun. 11, 2020

(65) Prior Publication Data
US 2022/0016236 A1    Jan. 20, 2022

(30) Foreign Application Priority Data
Dec. 5, 2018 (KR) .................. 10-2018-0155084

(51) Int. Cl.
*A61K 39/00* (2006.01)
*A61K 39/23* (2006.01)
(Continued)

(52) U.S. Cl.
CPC .......... *A61K 39/23* (2013.01); *C12N 15/8509* (2013.01); *G01N 33/56983* (2013.01);
(Continued)

(58) Field of Classification Search
None
See application file for complete search history.

(56) References Cited

U.S. PATENT DOCUMENTS

| 5,498,413 A | 3/1996 | Casal Alvarez et al. |
| 2004/0093644 A1 | 5/2004 | Rymerson et al. |

(Continued)

FOREIGN PATENT DOCUMENTS

| CN | 102382845 A | 3/2012 |
| CN | 103936839 A | 7/2014 |

(Continued)

OTHER PUBLICATIONS

Jun. 28, 2018 (Jun. 28, 2018), "Porcine parvo virus (PPV) viral protein 2 encoding gene, SEQ 3.", XP002805515, retrieved from EBI accession No. GSN:BFF97790 Database accession No. BFF97790 * the whole document *.

(Continued)

*Primary Examiner* — M Franco G Salvoza
(74) *Attorney, Agent, or Firm* — Harness, Dickey & Pierce, P.L.C.

(57) ABSTRACT

The present invention provides: a recombinant expression vector comprising a gene encoding a porcine parvovirus VP2 protein; a recombinant plant or a recombinant insect cell transformed with the vector; and a vaccine composition for a porcine parvovirus and a composition for diagnosing (Continued)

porcine parvovirus, both of which contain a porcine parvovirus VP2 protein obtained from the recombinant plant or the recombinant insect cell. When the recombinant plant or recombinant insect cell of the present invention is used, the porcine parvovirus antigenic protein can be produced with high efficiency, and the porcine parvovirus antigenic protein production method using the recombinant plant or recombinant insect cell has excellent safety and stability compared with other antigen production methods.

8 Claims, 8 Drawing Sheets

Specification includes a Sequence Listing.

(51) Int. Cl.
*C12N 15/85* (2006.01)
*G01N 33/569* (2006.01)
*G01N 33/68* (2006.01)

(52) U.S. Cl.
CPC .... *G01N 33/6854* (2013.01); *A61K 2039/552* (2013.01); *C12N 2015/8518* (2013.01); *C12N 2750/14034* (2013.01); *G01N 2333/015* (2013.01); *G01N 2469/20* (2013.01)

(56) References Cited

U.S. PATENT DOCUMENTS

| | | | |
|---|---|---|---|
| 2017/0056492 | A1 | 3/2017 | Guelen et al. |
| 2018/0133309 | A1 | 5/2018 | Bucklin et al. |

FOREIGN PATENT DOCUMENTS

| | | | | |
|---|---|---|---|---|
| CN | 104561049 | A | 4/2015 | |
| CN | 107661496 | A | 2/2018 | |
| CN | 108410885 | A | 8/2018 | |
| KR | 10-0142210 | | 7/1998 | |
| KR | 20070045817 | A | 5/2007 | |
| KR | 20170068789 | A | 6/2017 | |
| WO | WO-0194392 | A2 * | 12/2001 | ........... C07K 14/005 |
| WO | WO-2006/107954 | A2 | 10/2006 | |
| WO | WO-2018/083156 | A1 | 5/2018 | |

OTHER PUBLICATIONS

Notice of Allowance for Japanese Patent Application No. 2021-532309, dated Dec. 5, 2022.
EESR for Europe Patent Application No. 19892393.0, dated Feb. 10, 2022.
International Search Report from corresponding PCT Application No. PCT/KR2019/015705, dated Mar. 16, 2020.
NCBI. Genbank accession No. JQ249927.1 (Sep. 4, 2012).
NCBI. Genbank accession No. AY684866.1 (Jan. 24, 2006).
Office Action from corresponding Chinese Application No. 201980080835.3, Dated Jul. 31, 2023.

* cited by examiner

| Amino acid VP2 | NA DL-2 | Kres se | Chall enge | IDT | Tor nau | T14 2 | 07 | 49 | 2-5 | 82 | 13-7 | 20-2 | 21-1 | 22-8 | 23-1 |
|---|---|---|---|---|---|---|---|---|---|---|---|---|---|---|---|
| | | | | | | | | | | | | | | | PPV virus |
| 28 | G | - | - | - | - | - | - | S | S | - | - | - | - | - | - |
| 45 | T | S | S | S | S | S | S | S | S | S | S | S | S | S | S |
| 143 | Q | - | - | - | - | - | - | R | - | - | - | - | - | - | - |
| 215 | I | T | - | T | T | T | T | T | T | T | T | T | T | T | T |
| 228 | Q | - | - | - | - | - | E | - | - | E | - | - | - | - | - |
| 270 | D | - | - | - | - | - | - | - | - | N | - | - | - | - | - |
| 320 | I | - | - | T | T | - | - | - | - | - | - | T | T | T | - |
| 378 | D | G | G | G | G | G | G | G | G | G | G | G | G | G | G |
| 383 | H | Q | Q | - | Q | Q | Q | Q | Q | Q | Q | Q | Q | Q | Q |
| 407 | K | - | - | N | N | - | - | R | R | - | R | - | - | - | - |
| 414 | A | - | - | - | - | - | S | T | T | S | - | - | - | - | - |
| 419 | E | - | - | - | - | - | Q | - | - | Q | - | - | - | - | - |
| 436 | S | P | P | P | P | P | T | T | T | T | P | P | P | P | P |
| 549 | T | - | - | - | - | - | - | A | - | - | - | - | - | - | - |
| 565 | R | K | K | K | K | K | K | K | K | K | K | K | K | K | K |
| 570 | Y | - | - | - | - | - | - | H | - | H | H | H | H | H | H |
| 579 | Y | - | - | - | - | - | - | - | - | - | - | - | Stop | Stop | - |

FIG. 1

[ Rbc-TP ]—[ 6XHis ]—[ PPV 82-opt VP2 ]

FIG. 2A

Lane 1: SF9 cells
Lane 2: PPV 07-opt

RECOMBINANT PORCINE PARVOVIRUS ANTIGENIC PROTEIN AND USE THEREOF

CROSS-REFERENCE TO RELATED APPLICATIONS

This application is a national phase application of PCT Application No. PCT/KR2019/015705, filed on Nov. 15, 2019, which claims the benefit of and priority to Korean Patent Application No. 10-2018-0155084, filed on Dec. 5, 2018. The entire disclosures of the applications identified in this paragraph are incorporated herein by references.

TECHNICAL FIELD

The present disclosure was made with the support of the Ministry of Agriculture, Food, and Rural Affairs, Republic of Korea, under Project No. 1545016316, which was conducted in the research project named "Development of new porcine parvovirus vaccine using plant expression system" in the research program titled "Animal, plant quarantine and inspection technology development (R & D)" by the Animal and Plant Quarantine Agency, under management of the Animal and Plant Quarantine Agency, from 1 Jan. 2018 to 31 Dec. 2018.

The present disclosure relates to a recombinant porcine parvovirus antigenic protein and use thereof.

BACKGROUND ART

Porcine parvovirus (PPV), which has small DNA with a size of about 5 kb which is a non-enveloped, single-stranded, is one of the causes of reproductive disorders in pigs. Since porcine parvovirus was first isolated in Germany in 1965, porcine parvovirus is still prevalent around the world, including Europe and Asia. PPV serotype 1 is mainly associated with reproductive disorders, and representative clinical symptoms thereof include stillbirth, mummification, embryonic death, and infertility, which are called SMEDI syndrome. PPV causes skin diseases, diarrhea, and respiratory disorders in addition to reproductive disorders, thereby causing heavy economic losses to the pig industry.

Porcine parvovirus infections cause reproductive disorders in sows and thus are many problems worldwide, but are still not eradicated. Therefore, in order to minimize the loss of productivity and increase the fertility rate of pregnant sows in pig farms, novel vaccines with excellent efficacy and improved effectiveness are required.

Currently used porcine parvovirus infection diagnostic methods encompass virus neutralization test (VNT), enzyme linked immunosorbent assay (ELISA), hemagglutination inhibition (HI), and the like. Solutions for hemagglutination inhibition assay (HIA) are suggested as assay solutions that are supplied for serum tests and disease diagnosis for livestock in current municipal animal disease control projects. HIA is cumbersome to use since blood cells of an animal (guinea pig) need to be used, and animals always need to be raised to collect blood cells. The virus neutralization test has problems in that porcine parvovirus needs to be grown in a clean bench and 3 to 4 days are required to obtain results.

SUMMARY

Technical Problem

The present inventors made intensive research efforts to develop, as an antigenic protein, a recombinant porcine parvovirus antigenic protein having excellent antigenicity and immunogenicity. As a result, the present inventors synthesized porcine parvovirus VP2 gene through codon optimization and established that a porcine parvovirus VP2 antigenic protein obtained from a recombinant plant or a recombinant insect cell transformed by a recombinant expression vector comprising the porcine parvovirus VP2 gene has high stability and immunogenicity, and thus completed the present disclosure.

Accordingly, an aspect of the present disclosure is to provide a recombinant porcine parvovirus VP2 protein expression vector.

Another aspect of the present disclosure is to provide a recombinant plant or recombinant insect cell expressing a recombinant porcine parvovirus VP2 protein.

Still another aspect of the present invention is to provide a vaccine composition for porcine parvovirus.

Still another aspect of the present invention is to provide a composition for diagnosis of porcine parvovirus.

Still another aspect of the present invention is to provide a kit for diagnosis of porcine parvovirus.

Still another aspect of the present invention is to provide a method for diagnosis of porcine parvovirus.

Technical Solution

In accordance with an aspect of the present disclosure, there is provided a recombinant expression vector comprising a gene encoding a porcine parvovirus VP2 protein.

The present inventors made intensive research efforts to develop, as an antigenic protein, a recombinant porcine parvovirus antigenic protein having excellent antigenicity and immunogenicity. As a result, the present inventors synthesized porcine parvovirus VP2 gene through codon optimization and established that a porcine parvovirus VP2 antigenic protein obtained from a recombinant plant or a recombinant insect cell transformed by a recombinant expression vector comprising the porcine parvovirus VP2 gene has high stability and immunogenicity.

The gene encoding the porcine parvovirus VP2 protein may be expressed by the nucleotide sequence of SEQ ID NO: 3 or 4 or may have a nucleotide sequence functionally equivalent thereto.

The nucleotide sequence of SEQ ID NO: 3 is a sequence that optimize the codons of the porcine parvovirus 82 VP2 gene for plant expression.

The nucleotide sequence of SEQ ID NO: 4 is a sequence that optimize the codons of the porcine parvovirus 07 VP2 gene for plant expression.

The term "functionally equivalent" refers to having at least 70%, preferably at least 80%, more preferably at least 90%, still more preferably at least 95% sequence homology to the nucleotide sequence of SEQ ID NO:3 or 4 as a result of addition, substitution, or deletion of nucleotides, and means a nucleotide sequence exhibiting substantially the same physiological activity as the protein coded by the nucleotide sequence set forth in SEQ ID NO: 3 or 4. For example, some nucleotide sequences are modified by deletion, substitution, or insertion, but may include variants which may make the functionally the same action as the nucleic acid molecule encoding the porcine parvovirus VP2 protein.

In accordance with another aspect of the present disclosure, there is provided a recombinant plant transformed with the recombinant expression vector and expressing a porcine parvovirus VP2 protein.

The plant may be *Nicotiana* sp. plant.

The *Nicotiana* sp. plant may be *Nicotiana acuminata, Nicotiana africana, Nicotiana elate, Nicotiana attenuata, Nicotiana benthamiana, Nicotiana clevelandii, Nicotiana exigua, Nicotiana glauca, Nicotiana glutinosa* L., *Nicotiana langsdorffii, Nicotiana longiflora, Nicotiana occidentalis, Nicotiana obtusifolia, Nicotiana otophora, Nicotiana plumbaginifolia, Nicotiana quadrivalvis, Nicotiana rustica* L., *Nicotiana suaveolens* Lehm., *Nicotiana sylvestris, Nicotiana tabacum* L. or *Nicotiana tomentosiformis* Goodsp., and may be for example *Nicotiana benthamiana*.

The plant transformed with the recombinant expression vector comprising a gene encoding a porcine parvovirus VP2 protein according to the present disclosure may express the porcine parvovirus VP2 protein. When the transformed plant is used, a large amount of protein can be easily produced in a typical laboratory where plants can be cultivated; the obtained porcine parvovirus VP2 protein has a biological function inherent to the porcine parvovirus antigenic protein, such as hemagglutination ability for guinea pig red blood cell; safety is secured without the possibility of contamination caused by handling of infectious live viruses; and antigens can be mass-produced very promptly and accurately compared with a conventional antigen preparation process.

According to an embodiment of the present disclosure, the porcine parvovirus VP2 antigenic protein obtained from the recombinant plant can be advantageously used in diagnosis of porcine parvovirus.

In accordance with another aspect of the present disclosure, there is provided a recombinant insect cell transformed with the recombinant expression vector and expressing a porcine parvovirus VP2 protein.

The insect cell may be an Sf-9 cell derived from *Spodoptera frugiperda*, but is not limited thereto.

According to an embodiment of the present disclosure, although the porcine parvovirus VP2 gene contained in the recombinant expression vector is configured of a sequence optimized for plant expression, the porcine parvovirus VP2 protein is also effectively expressed in the recombinant insect cell transformed with the recombinant expression vector.

According to an embodiment of the present disclosure, the porcine parvovirus VP2 antigenic protein obtained from the recombinant insect cell can be advantageously used in diagnosis of porcine parvovirus.

In accordance with another aspect of the present disclosure, there is provided a composition and a kit each for diagnosis of porcine parvovirus, the composition and the kit each comprising a porcine parvovirus VP2 protein expressed by the recombinant plant or recombinant insect cell.

As used herein, the term "diagnosis" refers to the identification of the presence or characteristics of pathological conditions. For the purpose of the present disclosure, diagnosis is to identify the occurrence or nonoccurrence of porcine parvovirus or the possibility of occurrence thereof.

The diagnostic kit may be manufactured using a method commonly used in the art. Such a diagnostic kit includes a porcine parvovirus VP2 antigenic protein as well as instruments, reagents, and the like that are typically used in the art with respect to immunoassay. Examples of these instruments/reagents may include a suitable carrier, a labeling substance capable of generating a detectable signal, a solubilizing agent, a cleansing agent, a buffer, a stabilizer, and the like, but are not limited thereto. When the labeling substance is an enzyme, a substrate capable of measuring enzyme activity and a reaction terminator may be included. Examples of the suitable carrier include, but are not limited to, soluble carriers, for example, physiologically acceptable buffers well known in the art, e.g., PBS, insoluble carriers, for example, polystyrene, polyethylene, polypropylene, polyester, polyacrylonitrile, fluorine resin, crosslinked dextran, polysaccharides, and polymers, such as magnetic microparticles made of latex coated with a metal, paper, glass, metals, agarose, and combinations thereof.

Furthermore, the present disclosure provides a method for diagnosis of porcine parvovirus, wherein a porcine parvovirus VP2 antibody is detected through an antigen-antibody reaction in a sample, by using, as an antigen, the porcine parvovirus VP2 protein expressed by the recombinant plant or recombinant insect cell.

The antigen-antibody reaction may use all the methods that are typically used in the art, and may use, for example, at least one method selected from the group consisting of tissue immunostaining, radioactive immunoassay (RIA), enzyme immunoassay (ELISA), Western blotting, immunoprecipitation assay, immunodiffusion assay, complement fixation assay, fluorescence-activated cell sorter (FACS), and protein chip analysis.

Examples of the sample include, but are not limited to, cells, blood, urine, saliva, tissue, and the like, which are suspected of being infected with porcine parvovirus or are infected therewith.

In accordance with still another aspect of the present disclosure, there is provided a vaccine composition for porcine parvovirus, the vaccine composition comprising a porcine parvovirus VP2 protein expressed by a recombinant plant or recombinant insect cell transformed with a recombinant expression vector comprising a gene encoding the porcine parvovirus VP2 protein, the gene being represented by the nucleotide sequence of SEQ ID NO: 3 or 4.

As used herein, the "vaccine composition" refers to a composition that has a beneficial influence on an immune response of a subject. The vaccine composition provides the subject with a cellular immune response such as cytotoxic T lymphocyte (CTL), or a humoral immune response such as an enhanced systemic or local immune response induced by an antibody.

The vaccine composition may further contain a pharmaceutically acceptable carrier. The pharmaceutically acceptable carrier that may be contained in the composition of the present disclosure is ordinarily used at the time of formulation, and examples thereof include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like.

The composition of the present disclosure may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in Remington's Pharmaceutical Sciences (19th ed., 1995).

The vaccine composition of the present disclosure may contain other ingredients, such as a stabilizer, an excipient, other pharmaceutically acceptable compounds, or any other antigen or a portion thereof. The vaccine may be present in the form of a freeze-dried preparation or a suspension, all of which are common in the field of vaccine production.

The dosing form of the vaccine composition of the present disclosure may be that of an enteric coated dosage unit, an inoculum for intra-peritoneal, intramuscular or subcutaneous administration, an aerosol spray, by oral or intranasal application. Administration through drinking water or feed pellets is also possible.

In the vaccine composition of the present disclosure, immunomodulatory molecules, such as heterologous antigens and cytokines, may be delivered as a single vaccine while expressed in the same recombinant, and may be administered together with an immune adjuvant. As used herein, the term "immune adjuvant" generally refers to any material (e.g., alum, Freund's complete adjuvant, Freund's incomplete adjuvant, LPS, poly IC, poly AU, etc.) that increases body fluids or cellular immune responses against antigens.

Advantageous Effects

Features and advantages of the present disclosure are summarized as follows.

(a) The present invention provides: a recombinant expression vector comprising a gene encoding a porcine parvovirus VP2 protein; a recombinant plant or a recombinant insect cell transformed with the vector; and a vaccine composition for a porcine parvovirus and a composition for diagnosing porcine parvovirus, both of which contain a porcine parvovirus VP2 protein obtained from the recombinant plant or the recombinant insect cell.

(b) When the recombinant plant or recombinant insect cell of the present invention is used, the porcine parvovirus antigenic protein can be produced with high efficiency, and the porcine parvovirus antigenic protein production method using the recombinant plant or recombinant insect cell has excellent safety and stability compared with other antigen production methods.

(c) The composition for diagnosis of porcine parvovirus of the present disclosure uses a recombinant antigenic protein, and thus is safe due to the absence of the possibility of contamination caused by handling of live viruses and enables a prompt diagnosis of the infection with porcine parvovirus from a large amount of samples.

BRIEF DESCRIPTION OF THE DRAWINGS

FIG. 1 shows the sequence of VP2 protein for each porcine parvovirus strain.

FIG. 2A is a schematic diagram of a recombinant expression vector structure comprising a gene encoding PPV 82-opt VP2 protein.

Rbc:6His:VP2 represents the expression of PPV VP2 in plants transformed with an expression vector comprising RuBisCo transit peptide, 6×His, and codon-optimized PPV VP2 in sequence; and Rbc:VP2:6His represents the expression of PPV VP2 in plants transformed with an expression vector comprising RuBisCo transit peptide, codon-optimized PPV VP2, and 6×His in sequence.

Figure 3A:
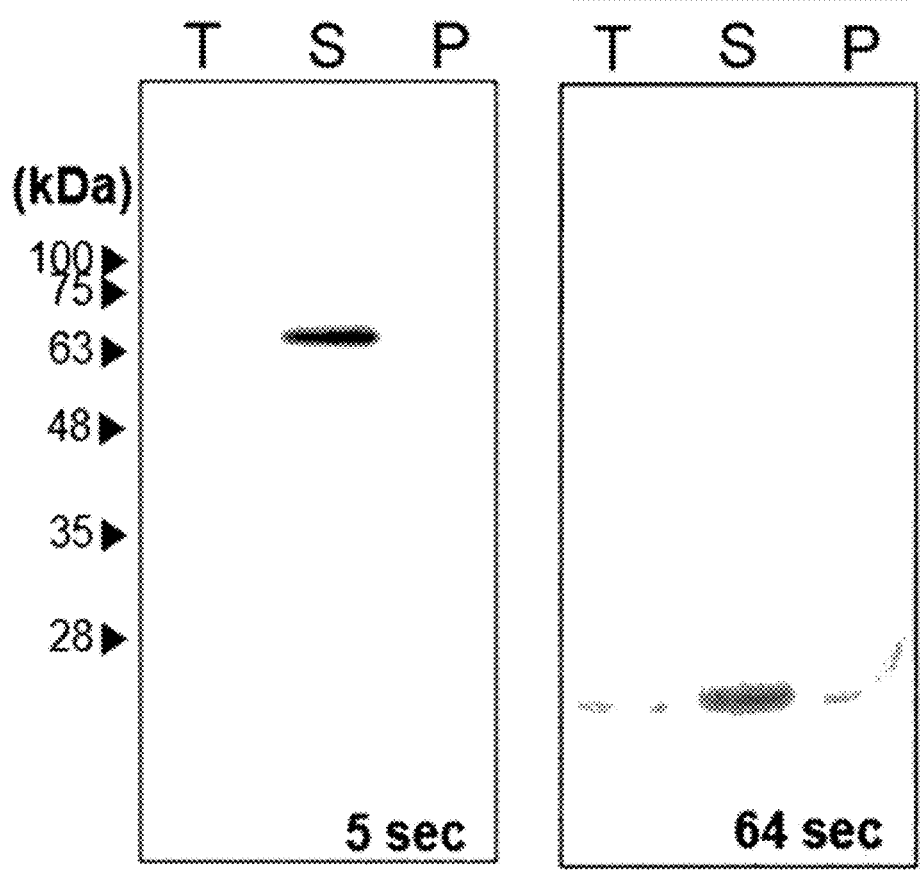
FIG. 3A shows the Western blotting results of recombinant PPV 82-opt VP2 proteins expressed in plants.
Figure 3B:
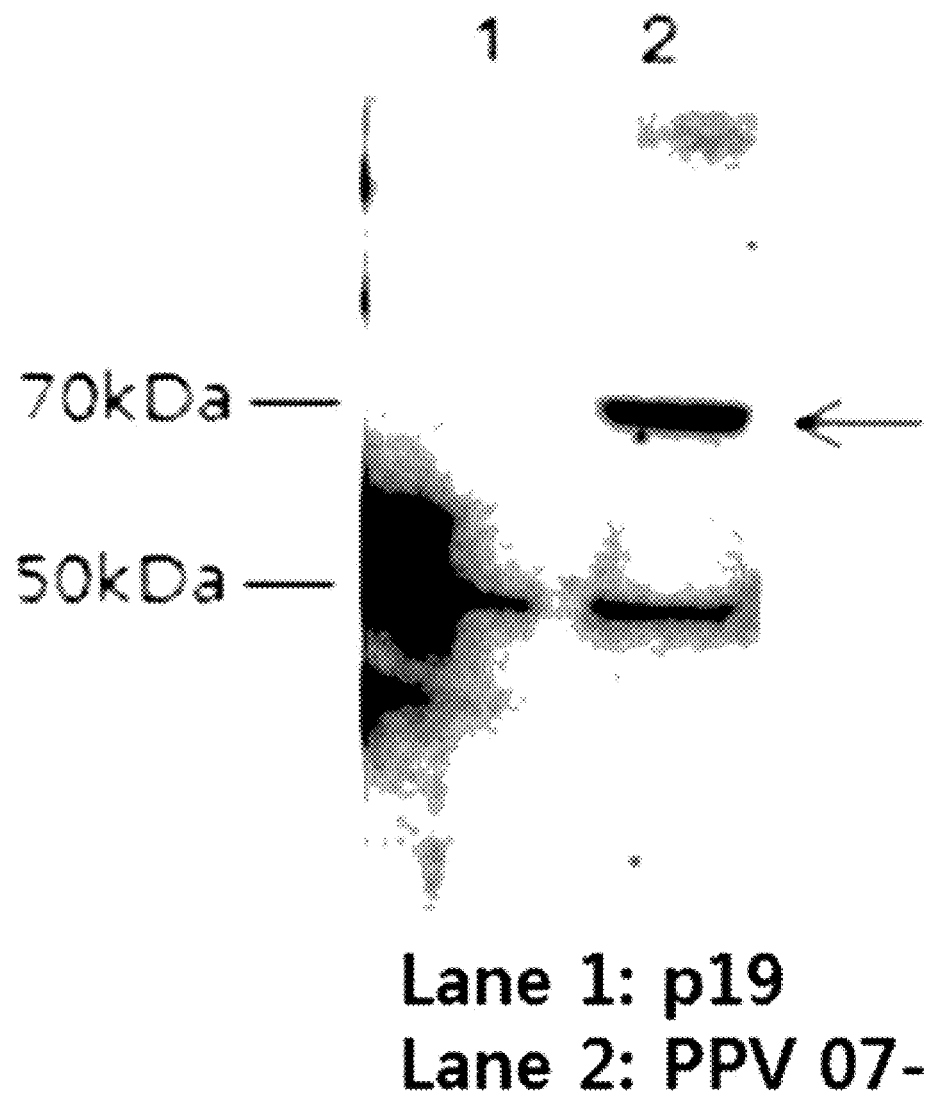

FIG. 3B shows the Western blotting results of recombinant PPV 07-opt VP2 protein expressed in plants.

Figure 3C:
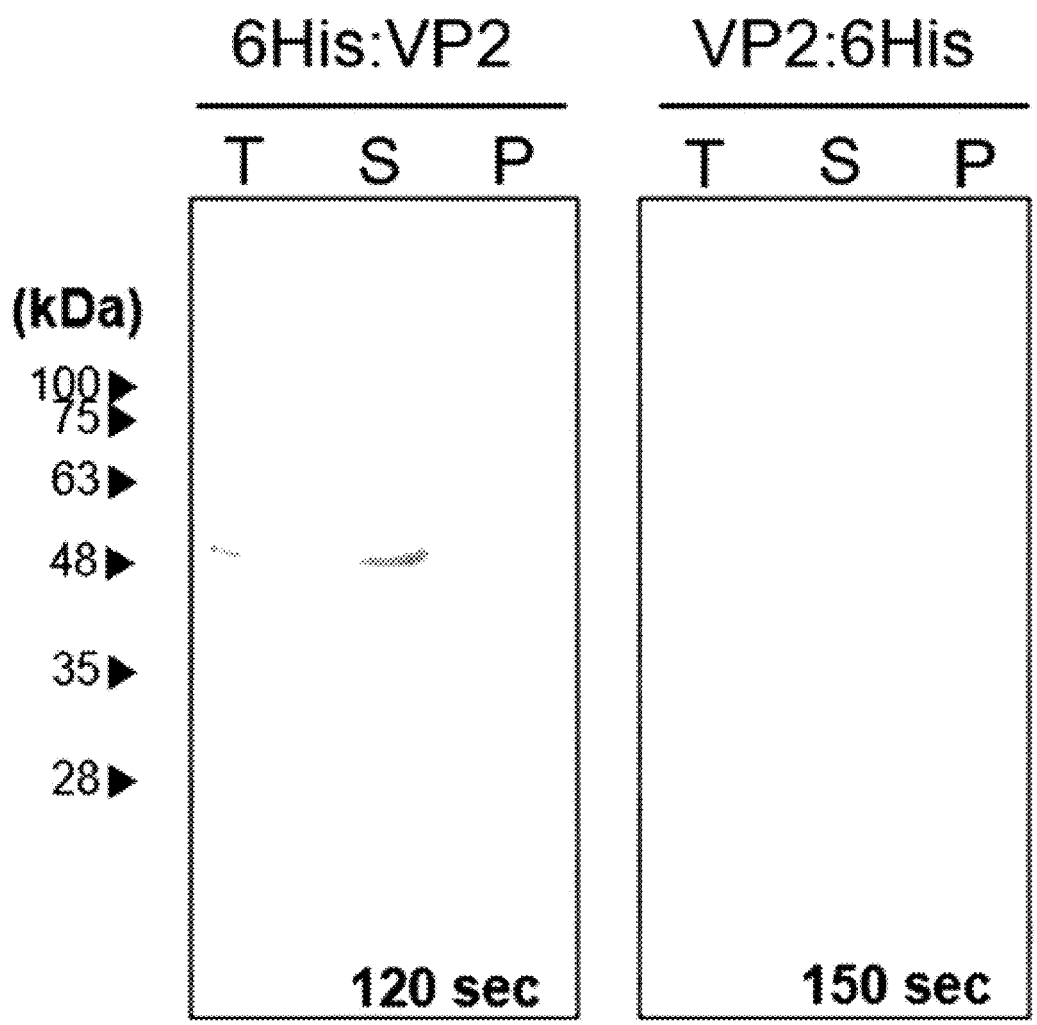

FIG. 3C shows the Western blotting results of PPV VP2 expression in plants transformed with expression vectors comprising non-codon-optimized PPV VP2.

6His:VP2 represents the expression of PPV VP2 in plants transformed with an expression vector comprising 6×His and non-codon-optimized PPV VP2; and VP2:6His represents the expression of PPV VP2 in plants transformed with an expression vector comprising non-codon-optimized PPV V2 and 6×His.

Figure 4:
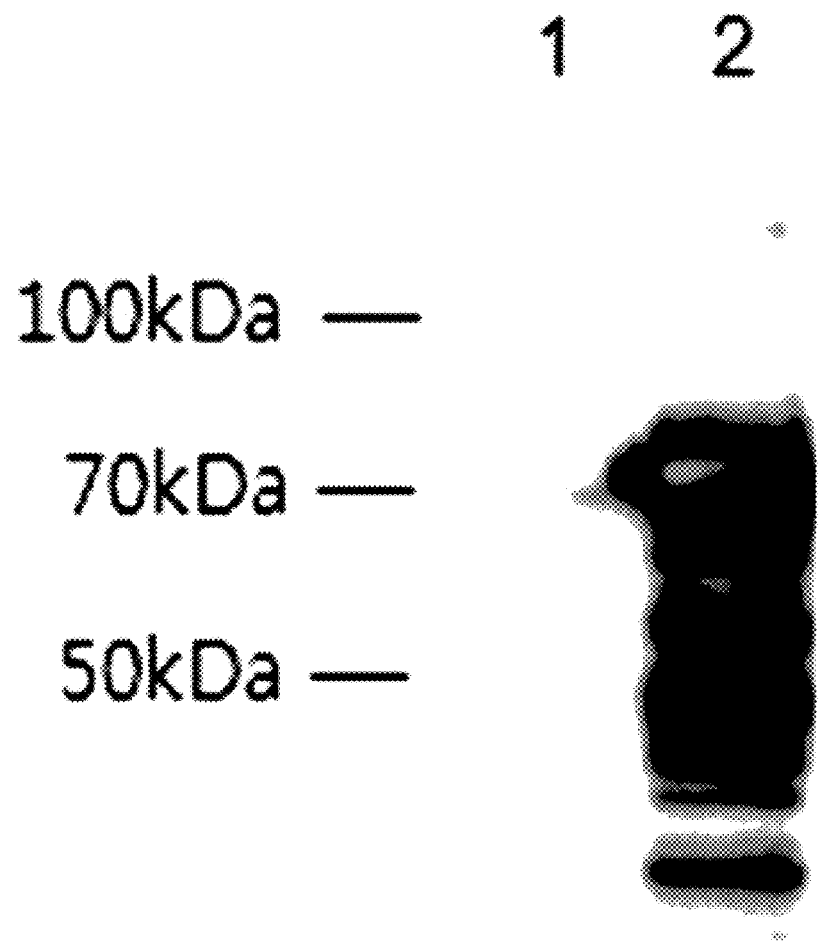

FIG. 4 shows the Western blotting results of recombinant PPV 07-opt VP2 protein expressed in insect cells.

Figure 5A:
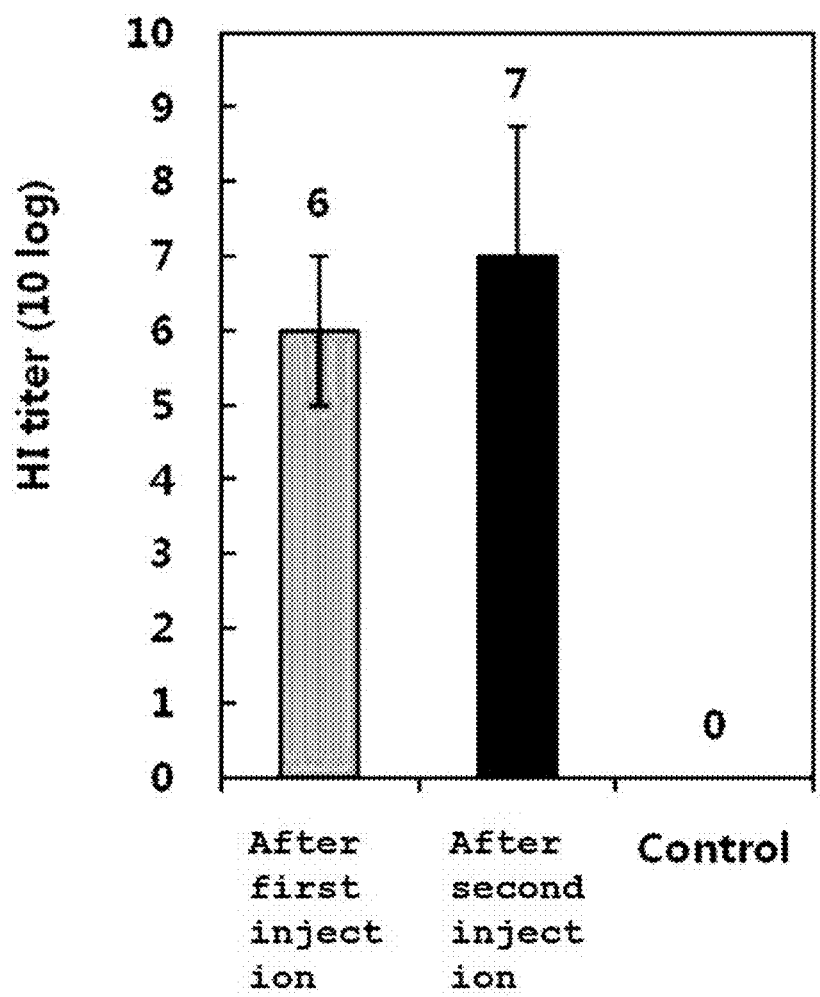

FIG. 5A shows the results of evaluating, in pigs, the immunogenicity of recombinant PPV 82-opt VP2 protein expressed in plants.

Figure 5B:
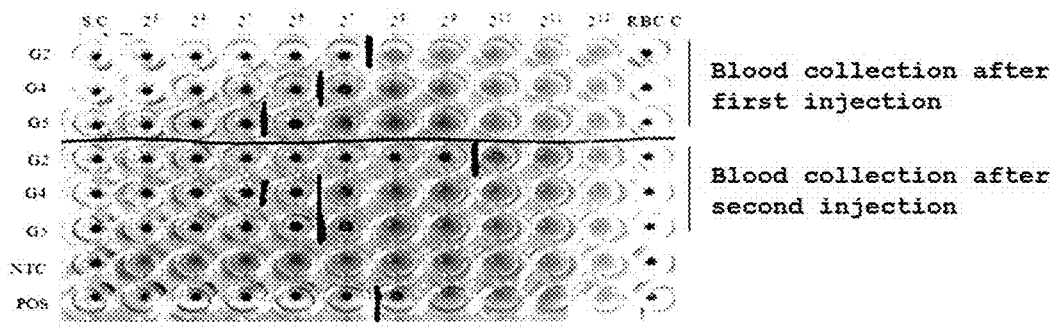

FIG. 5B shows the 96-well plate used in the evaluation of the immunogenicity of recombinant PPV 82-opt VP2 protein expressed in plants.

Figure 6A:
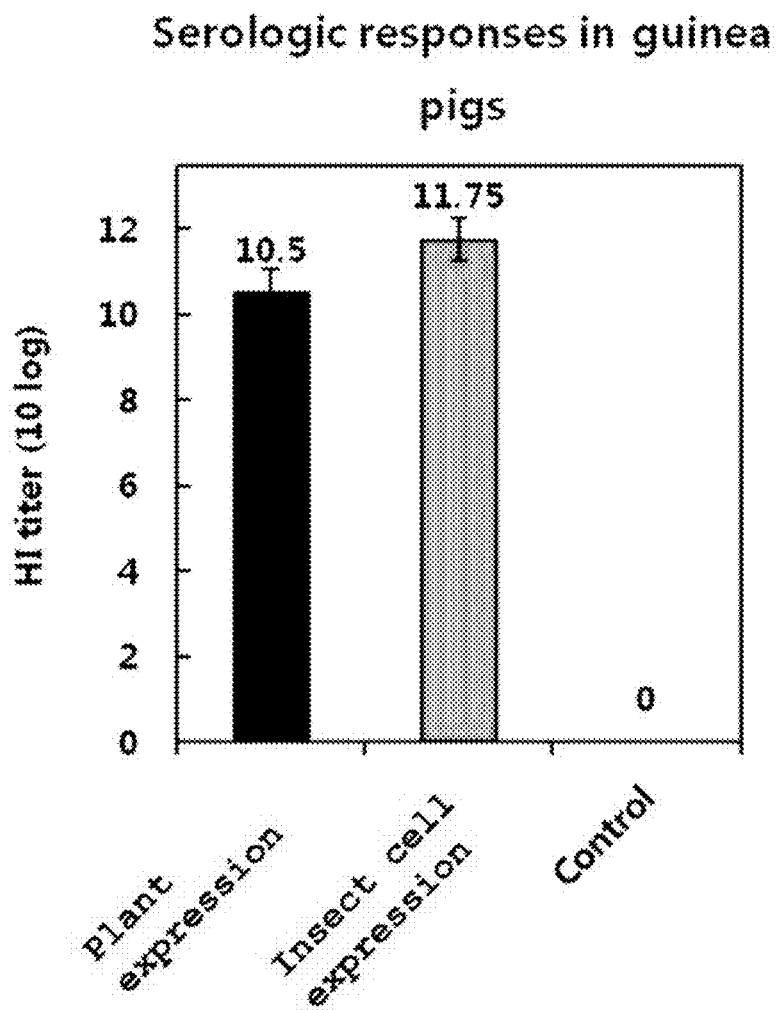

FIG. 6A shows the results of evaluating, in guinea pigs, the immunogenicity of recombinant PPV 07-opt VP2 protein expressed in plants and insect cells.

Figure 6B:
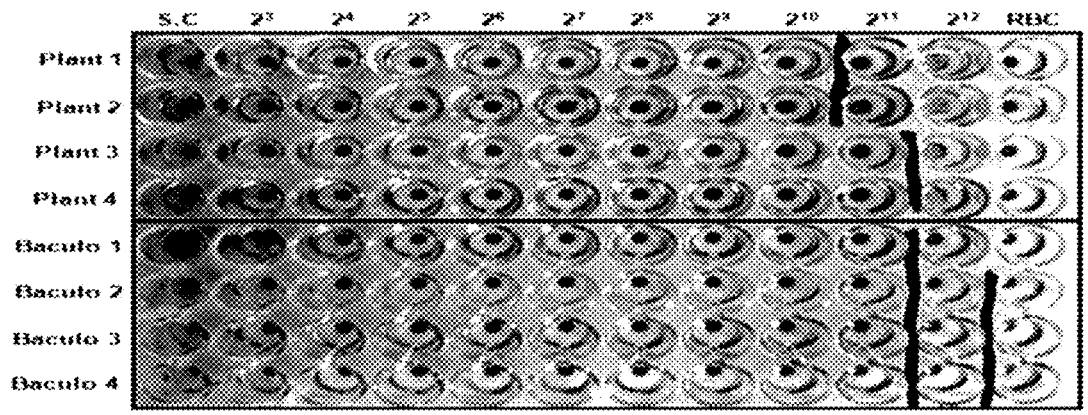

FIG. 6B shows the 96-well plate used in the evaluation of the immunogenicity of recombinant PPV 07-opt VP2 protein expressed in plants and insect cells.

Figure 7A:
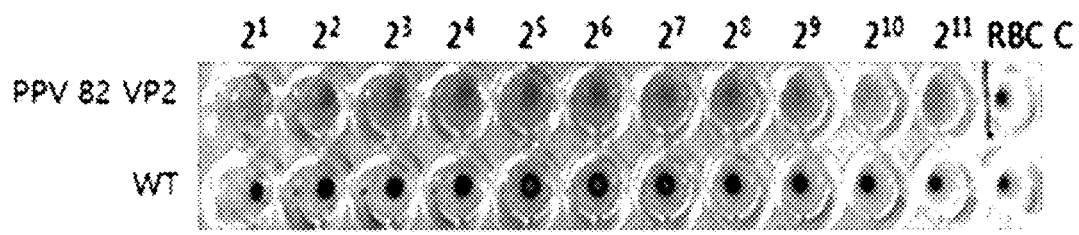

FIG. 7A shows the results of verifying, with respect to guinea pig red blood cells, the hemagglutination ability of recombinant PPV 82-opt VP2 protein expressed in plants.

Figure 7B:
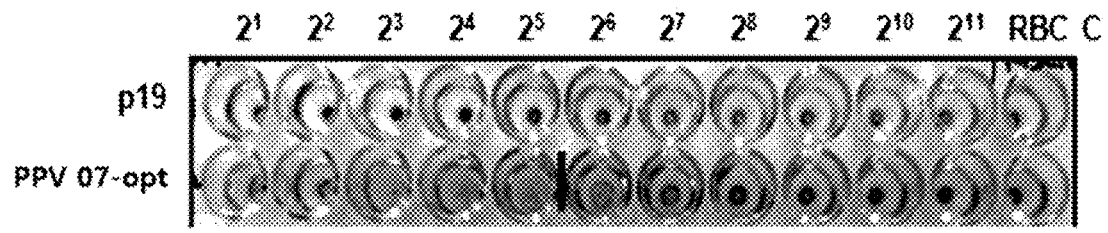

FIG. 7B shows the results of verifying, with respect to guinea pig red blood cells, the hemagglutination ability of recombinant PPV 07-opt VP2 protein expressed in plants.

DETAILED DESCRIPTION

Hereinafter, the present disclosure will be described in more detail with reference to examples. These examples are provided only for the purpose of illustrating the present disclosure in more detail, and therefore, according to the purpose of the present disclosure, it would be apparent to a person skilled in the art that these examples are not construed to limit the scope of the present disclosure.

EXAMPLES

Example 1: Construction of Recombinant Porcine Parvovirus (PPV) VP2 (PPV 82-Opt, PPV 07-Opt) Antigen Plant Expression Vectors To target VP2 having the highest antigenicity, the PPV VP2 DNA sequence obtained from specimens of the aborted and stillborn fetuses was used, and the sequence was optimized for *Nicotiana benthamiana* through the Genscript's codon optimization program, and synthesized by Bioneer company. The nucleotide sequences of the optimized PPV 82-opt VP2 and PPV 07-opt VP2 are composed of 1740 bp and 1737 bp, respectively.

1-1. Recombinant PPV 82-Opt VP2 Expression Vector

For plant expression of PPV VP2 antigens, the polynucleotide (SEQ ID NO: 1) encoding the RuBisCo transit peptide, the polynucleotide (SEQ ID NO: 2) encoding six consecutive histidine resides, and the polynucleotide (SEQ ID NO: 3) encoding PPV 82 VP2 protein were sequentially linked between the CaMV 35S promoter gene and the NOS terminator of the pCAMBIA1300 vector, thereby constructing a recombinant PPV 82-opt VP2 plant expression vector (FIG. 2A).

1-2. Recombinant PPV 07-Opt VP2 Expression Vector

Figure 2B:
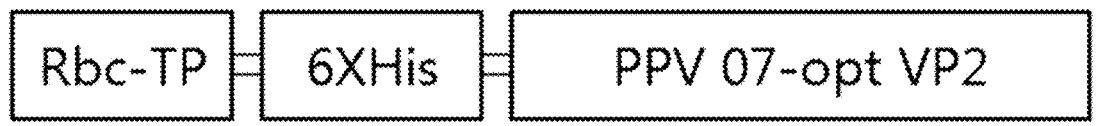
FIG. 2B is a schematic diagram of a recombinant expression vector structure comprising a gene encoding PPV 07-opt VP2 protein.

For plant expression of PPV VP2 antigens, the polynucleotide (SEQ ID NO: 1) encoding the RuBisCo transit peptide, the polynucleotide (SEQ ID NO: 2) encoding six consecutive histidine resides, and the polynucleotide (SEQ ID NO: 4) encoding PPV 07 VP2 protein were sequentially linked between the CaMV 35S promoter gene and the NOS terminator of the pCAMBIA1300 vector, thereby constructing a recombinant PPV 07-opt VP2 plant expression vector (FIG. 2B).

Example 2: Expression of Recombinant PPV VP2 (PPV 82-Opt, PPV 07-Opt) Protein in Plants To express recombinant PPV 82-opt VP2 or PPV 07-opt VP2 protein in plants, the recombinant expression vectors prepared in Example 1 were transformed into the *agrobacterium* strain GV3101 through electroporation using Gene Pulser XCell (Bio-Rad, USA) according to the manufacturer's instructions. The transformed GV3101 cells were grown in YEP medium (10 g of yeast extract, 10 g of peptone, 5 g of NaCl, 50 mg/L kanamycin, and 25 mg/L rifampicin) comprising an appropriate antibiotic until the cells reach a stationary phase. The cultures were centrifuged, and precipitates were re-suspended in an infiltration media (10 mM MES, 10 mM $MgCl_2$, and 100 mM acetosyringone) to an $OD_{600}$ of 0.5, and then incubated at room temperature for 1 hour. Agro-infiltration was performed by infiltrating the *Agrobacterium* suspension into *Nicotiana benthamiana* leaves grown to the age of 4-6 weeks under the condition of 25° C. through a syringe or by vacuum infiltration.

Example 3: Verification of Expression of Recombinant Porcine PPV VP2 (PPV 82-Opt, PPV 07-Opt) Protein in Plants The leaf tissue with a size of about 3 $cm^2$ was ground using 100 μl of a grinding buffer (20 mM Tris-HCl (pH 7.5), 150 mM NaCl, 1 mM EDTA, 1% Triton X-100, 0.1% SDS, 5 mM DTT, and plant protease inhibitor cocktail [Sigma-Aldrich]), and the insoluble debris was centrifuged at 20,000×g for 10 minutes at 4° C. The sample was subjected to separation on 12% SDS-PAGE gels, and transferred onto PVDF membranes (Millipore Merck KGaA of Darmstadt, Germany). Then, the sample was incubated with monoclonal His antibody (1:1,000 dilution, Invitrogen) and detected by the chemiluminescent substrate.

The use of the plant expression vector constructed by linking, in sequence, the polynucleotide encoding RubisCo transit peptide, the polynucleotides encoding six consecutive histidine residues, and the polynucleotides encoding porcine parvovirus VP2 protein (PPV 82-opt VP2 protein or PPV 07-opt VP2 protein) resulted in favorable expressions as confirmed in FIG. 3A (left panel) and FIG. 3B, but the use of the plant expression vector, constructed by linking histidines to the rear end of the porcine parvovirus VP2 protein, resulted in unfavorable protein expression (FIG. 3A, right panel).

The porcine parvovirus VP2 was not expressed in the plants transformed with the expression vectors comprising non-codon-optimized porcine parvovirus VP2 (FIG. 3C).

Example 4: Construction of Recombinant PPV 07-Opt VP2 Antigen Insect Cell Expression Vector The PPV 07-opt VP2 sequence was amplified, cloned into a pDrive vector, and then sequenced. For Baculovirus recombinant expression, cloning was performed using pFastBac™ HT B vector (Invitrogen Company).

Example 5: Expression and Verification of Recombinant PPV 07-Opt VP2 Protein in Insect Cells In order to express the recombinant PPV 07-opt VP2 protein in an insect, the recombinant expression vector was transformed into DH10Bac through heat shock at 42° C. according to the manufacturer's instructions. The transformed DH10Bac was incubated in S.O.C media for 4 hours at 37° C. The culture was diluted to 1/10, and incubated in LB media supplemented with gentamycin (7 ug/ml) antibiotic at 37° C. for 48 hours. After 10 colonies were transferred to 10 plates, the recombinant PPV 07-opt VP2 was sequenced using PCR with pUC/M13 primer. Sf-9 cells were transfected using Cellfectin II reagent (Invitrogen Company).

Transfection was performed at 27° C., and after five days, the cells were harvested, and protein extraction was performed at 4° C. for 30 minutes. Since the histidines were bound to the N-terminus of the recombinant PPV VP2 protein, the protein was separated using NI-NTA resin, for purification of the VP2 protein.

The purified protein was transferred onto a PVDF membrane, and then the membrane was blocked with 5% BSA. The membrane was incubated with the primary antibody mouse-His (1:1,000) at room temperature for 1 hour, followed by washing with TBST five times, and then incubated with the second antibody mouse-HRP (1:5,000) at room temperature for 1 hour, followed by washing with TBST five times, and then protein expression was visualized by the enhanced chemiluminescence (ECL) reaction (FIG. 4).

Example 6: Evaluation of Immunogenicity of Recombinant PPV VP2 Proteins 6-1. Evaluation of Immunogenicity of Recombinant PPV 82-Opt VP2 Protein The recombinant PPV 82-opt VP2 protein expressed in plants was mixed with an aluminum hydroxide gel adjuvant at 1:1, and 100-110 days old pigs were subjected to primary injection with 25,000 HA unit and, after two weeks, secondary injection. After two weeks, the blood was collected to measure the HI titer. As a result, a mean antibody titer of $2^7$ was confirmed (FIGS. 5A and 5B).

6-2. Evaluation of Immunogenicity of Recombinant PPV 07-OP VP2 Proteins

Guinea pigs were subjected to first injection with the recombinant PPV 07-opt VP2 protein expressed in the insect cells and the recombinant PPV 07-opt VP2 protein expressed using the plant expression system, in 500 HA unit each and, after two weeks, second injection. After two weeks, the blood was collected to measure the HI titer. As a result, the recombinant PPV 07-opt VP2 protein expressed in plants showed a mean antibody titer of $2^{10}$, and the recombinant PPV 07-opt VP2 protein expressed in the insect cells showed a mean antibody titer of $2^{11}$ (FIGS. 6A and 6B).

Example 7: Hemagglutination Assay (HA)

7-1. Hemagglutination Ability of Recombinant PPV 82-Opt VP2 Protein

PPV is characterized by agglutination with guinea pig red blood cells, and hemagglutination reaction was conducted referring to literature by Senda et al. (1986). The PPV 82-opt VP2 protein expressed in *Nicotiana benthamiana* was diluted to 2-fold in the 96-well U plate, mixed with 0.6% guinea pig red blood cells, and incubated at 37° C. for 1 hour, and then the results were analyzed.

The recombinant PPV 82-opt VP2 protein showed $2^{11}$ HA unit (8 g/plant) in terms of hemagglutination ability with guinea pig red blood cells, which verified antigenicity of the recombinant PPV 82-opt VP2 protein expressed in plants (Table 1 and FIG. 7A).

TABLE 1

| Classification | Hemagglutination ability with guinea pig red blood cells (Hemagglutination assay, HA) |
|---|---|
| *Nicotiana benthamiana* (negative control) | 0 |
| Recombinant PPV 82-opt VP2 protein extracted from plants | $2^{11}$(2048) |

7-2. Hemagglutination Ability of Recombinant PPV 07-Opt VP2 Protein

PPV is characterized by agglutination with guinea pig red blood cells, and hemagglutination reaction was conducted referring to literature by Senda et al. (1986). The PPV 07-opt VP2 protein expressed in *Nicotiana benthamiana* was diluted to 2-fold in the 96-well U plate, mixed with 0.6% guinea pig red blood cells, and incubated at 37° C. for 1 hour, and then the results were analyzed.

The recombinant PPV 07-opt VP2 protein showed $2^5$ HA unit (8 g/plant) in terms of hemagglutination ability with guinea pig red blood cells, which verified antigenicity of the recombinant PPV 07-opt VP2 protein expressed in plants (Table 2 and FIG. 7B).

TABLE 2

| Classification | Hemagglutination ability with guinea pig red blood cells (Hemagglutination assay, HA) |
|---|---|
| *Nicotiana benthamiana* (negative control) | 0 |
| Recombinant PPV 07-opt VP2 protein extracted from plants | $2^5$(32) |

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A recombinant expression vector comprising a gene encoding a porcine parvovirus (PPV) VP2 protein, wherein said gene comprises SEQ ID NO: 3 or 4.

2. A recombinant plant expressing a porcine parvovirus VP2 protein, transformed with the recombinant expression vector of claim 1.

3. The recombinant plant of claim 2, wherein the plant is *Nicotiana* sp. plant.

4. The recombinant plant of claim 3, wherein the *Nicotiana* sp. plant is at least one selected from the group consisting of *Nicotiana acuminata, Nicotiana africana, Nicotiana alata, Nicotiana attenuata, Nicotiana benthamiana, Nicotiana clevelandii, Nicotiana exigua, Nicotiana glauca, Nicotiana glutinosa* L., *Nicotiana langsdorffii, Nicotiana longiflora, Nicotiana occidentalis, Nicotiana obtusifolia, Nicotiana otophora, Nicotiana plumbaginifolia, Nicotiana quadrivalvis, Nicotiana rustica* L., *Nicotiana suaveolens* Lehm., *Nicotiana sylvestris, Nicotiana tabacum* L. and *Nicotiana tomentosiformis* Goodsp.

5. The recombinant plant of claim 4, wherein the *Nicotiana* sp. plant is *Nicotiana benthamiana*.

6. A recombinant insect cell expressing a porcine parvovirus VP2 protein, transformed with the recombinant expression vector of claim 1.

7. The recombinant insect cell of claim 6, wherein the insect cell is Sf-9 cell.

8. The recombinant insect cell of claim 7, wherein the Sf-9 cell is derived from *Spodoptera frugiperda*.

* * * * *

SEQUENCE LISTING

```
<160> NUMBER OF SEQ ID NOS: 6

<210> SEQ ID NO 1
<211> LENGTH: 231
<212> TYPE: DNA
<213> ORGANISM: Artificial Sequence
<220> FEATURE:
<223> OTHER INFORMATION: DNA sequence of Rubisco transit peptide

<400> SEQUENCE: 1
atggcttcct ctatgctctc ttccgctact atggttgcct ctccggctca ggccactatg      60
gtcgctcctt tcaacggact taagtcctcc gctgccttcc cagccacccg caaggctaac     120
aacgacacta cttccatcac aagcaacggc ggaagagtta actgcatgca ggtgtggcct     180
ccgattggaa agaagaagtt tgagactctc tcttaccttc ctgaccttac c              231

<210> SEQ ID NO 2
<211> LENGTH: 18
<212> TYPE: DNA
<213> ORGANISM: Artificial Sequence
<220> FEATURE:
<223> OTHER INFORMATION: DNA sequence of 6XHis

<400> SEQUENCE: 2
caccaccatc accaccat                                                    18

<210> SEQ ID NO 3
<211> LENGTH: 1740
<212> TYPE: DNA
<213> ORGANISM: Artificial Sequence
<220> FEATURE:
<223> OTHER INFORMATION: PPV 82 VP2 Nicotiana Benthamiana optimized
      sequence

<400> SEQUENCE: 3
atgagcgaga atgttgaaca cacaaccccc ataaacgccg ggacagaact ctcagctacc      60
gggaacgaaa gcgggggcgg tggcggaggg ggtggcggga ggggtgccgg agggggtgggc    120 gtgtcaacgg gtagtttcaa caaccaaaca gaatttcagt acctcgggga ggggttggtc    180
```

-continued

```
agaatcaccg cccacgcttc caggctcatc cacctcaata tgccagaaca cgaaacatat    240
aaacgtatcc atgtattaaa ttcagagtct ggagtggcag ggcaaatggt acaagatgat    300
gctcatacgc agatggtgac accgtggtca ttgatcgacg ctaacgcatg ggcgtttgg    360 ttcaatcccg cagattggca attgattagt aacaacatga ctgaaattaa ccttgtgagt    420
tttgaacagg agatattcaa cgtggtactg aagacaataa cagaaagtgc cacttcacct    480
cctactaaaa tatacaacaa cgatcttacc gcatccctta tggtagcatt agataccaat    540
aacacgttgc cttatactcc ggcagccccc cgttccgaga ctttggggtt ctatccgtgg    600
cttccaacta agccaacaca atataggtac tatttaagtt gcaccagaaa cttaaatccc    660
ccgacttata ccgggcagtc tgagcaaata acggattcaa tccaaactgg gctgcactct    720
gacatcatgt tttacactat tgagaacgct gttcctatac atttacttag aacaggagat    780
gaatttagca cagggatcta tcatttcaat acaaaaccct tgaaacttac gcattcttgg    840
cagacaaata ggagcctcgg ccttccgcct aagttgttaa ccgagccaac caccgaaggg    900
gaccaacacc ctggcacatt accagcagca aatacgagga agggctacca tcaaaccata    960
aataactcat acacagaagc tactgcaatt aggcctgccc aagttggcta caacaccccc   1020
tatatgaact ttgagtatag caatgggggg ccatttctta caccgatagt acctacggca   1080
gacacacagt ataacgatga tgaaccaaat ggtgctataa gattcacgat ggggtaccaa   1140
catggtcaac tcacgacttc ttcacaagaa ttagaaagat ataccttcaa tcctcaaagc   1200
aagtgcggcc gagccccgaa gcaacagttc aatcaacaat ccccactcaa tcttcaaaac   1260
actaacaacg gaacactgct tccgagtgat ccaattggag ggaaaactaa catgcacttc   1320
atgaacacct taaacacata cggacccctg acagcactca acaacaccgc tccagtgttc   1380
ccgaacggcc agatctggga caaagagttg gatactgatt taaaacctag acttcacgtt   1440
acggcccctt tcgtatgcaa aaacaaccct ccgggtcagc tttttgttaa gattgcccca   1500
aacttgacag atgactttaa tgctgacagc cccaacagc cacgaattat cacgtactcc   1560
aacttttggt ggaagggtac tctgacattc accgccaaga tgaggtccag taacatgtgg   1620
aatccaatac aacagcacac caccactgct gagaacatcg gaaactatat ccccacgaac   1680
attggaggga taaagatgtt tccagagcat agtcaactca ttcctagaaa gttatactag   1740
```

<210> SEQ ID NO 4
<211> LENGTH: 1737
<212> TYPE: DNA
<213> ORGANISM: Artificial Sequence
<220> FEATURE:
<223> OTHER INFORMATION: PPV 07 VP2 Nicotiana Benthamiana optimized sequence

<400> SEQUENCE: 4

```
atgagtgaga acgtggagca gcataatcca attaatgcag ggaccgaatt gtctgccacg     60
ggaaatgaaa gtgggggagg gggcggaggg ggtggaggac gaggtgcagg aggagtcgga    120
gtttccacgg gctcattcaa taaccagact gaatttcaat atcttggcga gggtctcgtt    180
cgaattaccg ctcatgccag ccgtctcatc cacctcaaca tgccggagca tgagacttat    240
aagagaatac atgtcctgaa tagcgagagt ggagttgccg gccaaatggt acaggatgat    300
gctcacactc aaatggtcac gccgtggtca ttaattgatg ccaacgcatg ggagtctgg    360 ttcaacccgg ctgactggca gcttatttct aacaacatga ccgagatcaa tttagttagc    420
tttgaacaag agatttttaa tgttgtcctg aagaccataa cggagtctgc cacgagtccc    480
```

-continued cccaccaaaa tctataacaa cgatctcaca gcaagcttga tggtggcatt agatactaac 540
aatacgttac cttacacacc cgcagccccg cgttcagaaa cattgggatt ctacccttgg 600
ttaccgacaa agccaacaca atataggtat tacctcagct gcactcgtaa tttaaacccg 660
ccaacatata cggggcaaag cgagcagatt acggacagca tacaaaccgg cttgcactca 720
gatattatgt tctatacgat cgaaaatgca gttcctattc atctgcttag gacaggtgat 780
gagttctcca caggtatata ccacttcgac actaaaccct taaaacttac tcacagttgg 840
cagaccaata gatctctggg cctccctcct aagttgctta ccgagcccac cacggaggga 900
gatcaacacc ccggaacttt accagcagcc aacacgcgaa agggatatca tcagacaatt 960
aataatagct acacagaggc cactgctatt aggccagccc aagttggata caacaccccg 1020
tatatgaatt ttgaatattc aaatggtgga cccttcttaa cacctattgt ccctacagca 1080
gatactcaat ataatgatga tgagccgaac ggtgcaatta ggttcactat gggctatcaa 1140
catgggcaac tcaccaccag cagtcaagaa ctcgagaggt atacgtttaa cccgcaatcc 1200
aagtgcggta gagcacctaa acaacagttc aatcaacaga gccctttaaa tctgcagaac 1260
acaaataacg ggactttgct gcctagtgac ccaataggag gcaagaccaa catgcatttt 1320
atgaacactc ttaacaccta tggaccgttg actgccctta ataataccgc tccagtattt 1380
ccaaacggcc agatctggga caaggagttg gacacagact tgaaacccag gttacacgtc 1440
actgcacctt ttgtctgcaa aaataatccc cccggacagc tttttgttaa gattgccccc 1500
aaccttaccg acgacttcaa tgccgactcc cctcagcaac caagaataat cacctatagc 1560
aatttctggt ggaaaggcac cttaacattc accgcaaaaa tgcgtagcag caatatgtgg 1620
aatccgatcc agcaacacac gacaactgct gagaatatcg ggaattatat tccaacgaat 1680
attgggggca taaagatgtt ccctgagtat tctcaactta tcccccgtaa gttgtac 1737

<210> SEQ ID NO 5
<211> LENGTH: 1740
<212> TYPE: DNA
<213> ORGANISM: Artificial Sequence
<220> FEATURE:
<223> OTHER INFORMATION: PPV 82 VP2 original sequence

<400> SEQUENCE: 5
atgagtgaaa atgtggaaca acacaaccct attaatgcag gcactgaatt gtctgcaaca 60
ggaaatgaat ctggggggtgg gggcggcggt ggcgggggta ggggtgctgg gggggttggt 120
gtgtctacag gtagtttcaa taatcaaaca gaatttcaat acttggggga gggcttggtt 180
agaatcactg cacacgcatc aagactcata catctaaata tgccagaaca cgaaacatac 240
aaaagaatac atgtactaaa ctcagaatca ggggtggcgg gacaaatggt acaagacgat 300
gcacacacac aaatggtaac accttggtca ctaatagatg ctaacgcatg ggggagtgtgg 360 ttcaatccag cggactggca gttaatatcc aacaacatga cagaaataaa cttagttagt 420
tttgaacaag aaatattcaa tgtagtgctt aaaacaatta cagaatcagc aacctcacca 480
ccaaccaaaa tatataataa tgatctaact gcaagcttaa tggtcgcact agacaccaat 540
aacacacttc catacacacc agcagcacct agaagtgaaa cacttggttt ttatccatgg 600
ttacctacaa aaccaactca atacagatat tacctatcat gcaccagaaa cctaaatcca 660
ccaacataca ctggacaatc agaacaaata acagactcaa tacaaacagg actacacagt 720
gacattatgt tctacacaat agaaaatgca gtaccaattc atcttctaag aacaggagat 780
gaattctcca caggaatata tcactttaac acaaaaccac taaaattaac tcactcatgg 840

```
caaacaaaca gatctctagg actgcctcca aaactactaa ctgaacctac cacagaagga    900
gaccaacacc caggaacact accagcagct aacacaagaa aaggttatca ccaaacaatt    960
aataatagct acacggaagc aacagcaatt aggccagctc aggtaggata taatacgcca   1020
tacatgaatt ttgaatactc caatggtgga ccatttctaa ctcctatagt accaacagca   1080
gacacacaat ataatgatga tgaaccaaat ggtgctataa gatttacaat gggttaccaa   1140
catggacaat taaccacatc ttcacaagag ctagaaagat acacattcaa tccacaaagt   1200
aaatgtggaa gagctccaaa gcaacaattt aatcaacagt caccactaaa cctacaaaat   1260
acaaataatg aacactttt  accttcagat ccaataggag aaaaactaa  catgcatttc   1320
atgaatacac tcaatacata tggaccatta acagcactaa acaatactgc acctgtattt   1380
ccaaatggtc aaatatggga taagaacttt gatacagatc taaaacctag actacatgtt   1440
acagctccat ttgtttgtaa aaacaatcca ccaggacaac tatttgtaaa aatagcacca   1500
aacctaacag atgatttcaa tgctgactct cctcaacaac ctagaataat aacttattca   1560
aactttt ggt ggaaaggaac actaacattc acagcaaaaa tgagatccag taatatgtgg   1620
aaccctattc aacaacacac aacaacagca gaaaacattg gtaactatat tcctacaaat   1680
attggtggca taaaaatgtt tccagaacat tcacaactta taccaagaaa attatactag   1740
```

<210> SEQ ID NO 6
<211> LENGTH: 1777
<212> TYPE: DNA
<213> ORGANISM: Artificial Sequence
<220> FEATURE:
<223> OTHER INFORMATION: PPV 07 VP2 original sequence
<400> SEQUENCE: 6

```
atgagtgaaa atgtggaaca acacaaccct attaatgcag gcactgaatt gtctgcaaca    60
ggaaatgaat ctgggggtgg gggcggcggt ggcgggggta ggggtgctgg ggggggttggt   120
gtgtctacag gtagtttcaa taatcaaaca gaatttcaat acttggggga gggcttggtt   180
agaatcactg cacacgcatc aagactcata catctaaata tgccagaaca cgaaacatac   240
aaaagaatac atgtactaaa ttcagaatca ggggtggcgg gacaaatggt acaagacgat   300
gcacacacac aaatggtaac accttggtca ctaatagatg ctaacgcatg ggggggtgtgg   360
ttcaatccag cagactggca gttaatatcc aacaacatga cagaaataaa cttagttagt   420
tttgaacaag aaatattcaa tgtagtactt aaaacaatta cagaatcagc aacctcacca   480
ccaaccaaaa tatataataa tgatctaact gcaagcttaa tggtagcact agacaccaat   540
aacacacttc catacacacc agcagcacct agaggtgaaa cacttggttt ttatccatgg   600
ttacctacaa aaccaactca atacagatat tacctatcat gcatcagaaa cctaaatcca   660
ccaacataca ctggacaatc acaacaaata acagacacaa tacaaacagg accacacagt   720
gacattatgt tctacacaat agaaaatgca gtaccaattc atcttctaag aacaggagat   780
gaattctcca caggaatata tcactttgac acaaaaccac taaaattaac tcactcatgg   840
caaacaaaca gatctctagg actgcctcca aaactactaa ctgaacctac cacagaagga   900
gaccaacacc caggaacact accagcagct aacacaagaa aaggttatca ccaaacaatg   960
aataatagct acacagaagc aacagcaatt aggccagctc aggtaggata taatacacca   1020
tacatgaatt ttgaatactc caatggtgga ccatttctaa ctcctatagt accaacagca   1080
gacacacaat ataatgatga tgaaccaaat ggtgctataa gatttacaat gggttaccaa   1140
```

-continued

```
catggacact taaccacatc ttcacaagag ctagaaagat acacattcaa tccacaaagt    1200
aaatgtggaa gagctccaaa gcaacaattt aatcaacagg caccactaaa cctagaaaat    1260
acaaataatg gaacacttttt accttcagat ccaataggag ggaaacctaa catgcatttc   1320
atgaatacac tcaatacata tggaccatta acagcactaa acaatactgc acctgtattt    1380
ccaaatggtc aaatatggga taaagaactt gatacagatc taaaacctag actacatgtt    1440
acagctccat ttgtttgtaa aaacaatcca ccaggacaac tatttgtaaa aatagcacca    1500
aacctaacag atgatttcaa tgctgactct cctcaacaac ctagaataat aacttattca    1560
aacttttggt ggaaaggaac actaacattc acagcaaaaa tgagatccag taatatgtgg    1620
aaccctattc aacaacacac aacaacagca gaaaacattg gtaactatat tcctacaaat    1680
attggtggca tgaaaatgtt tccagaatat tcacaactta taccaagaaa attatactag    1740
aaataactct gtaaataaaa actcagttac ttggtta                             1777
```